US009901338B2

(12) United States Patent
Anderson

(10) Patent No.: US 9,901,338 B2
(45) Date of Patent: Feb. 27, 2018

(54) SHAPE MEMORY COMPRESSION STAPLE

(71) Applicant: Biomet Manufacturing, LLC, Warsaw, IN (US)

(72) Inventor: David Anderson, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 593 days.

(21) Appl. No.: 14/547,791

(22) Filed: Nov. 19, 2014

(65) Prior Publication Data

US 2016/0135808 A1 May 19, 2016

(51) Int. Cl.
*A61B 17/06* (2006.01)
*A61B 17/064* (2006.01)
*A61B 17/00* (2006.01)

(52) U.S. Cl.
CPC ...... *A61B 17/0644* (2013.01); *A61B 17/0642* (2013.01); *A61B 2017/00867* (2013.01)

(58) Field of Classification Search
CPC .................................................. A61F 17/0644
See application file for complete search history.

(56) References Cited

U.S. PATENT DOCUMENTS

| | | | |
|---|---|---|---|
| 4,723,540 A | 2/1988 | Gilmer, Jr. | |
| 4,841,960 A | 6/1989 | Garner | |
| 4,848,328 A | 7/1989 | Laboureau et al. | |
| 4,852,558 A | 8/1989 | Outerbridge | |
| 4,994,063 A | 2/1991 | Garner | |
| 5,053,038 A | 10/1991 | Sheehan | |
| 5,089,009 A | 2/1992 | Green | |
| 5,454,814 A | 10/1995 | Comte | |
| 5,497,933 A | 3/1996 | DeFonzo et al. | |
| 5,593,423 A | 1/1997 | Person et al. | |
| 5,662,655 A | 9/1997 | Laboureau et al. | |
| 5,788,698 A | 8/1998 | Savornin | |
| 6,325,805 B1 | 12/2001 | Ogilvie et al. | |
| 6,447,517 B1 | 9/2002 | Bowman | |
| 6,461,365 B2 | 10/2002 | Bolduc et al. | |
| 6,685,708 B2 | 2/2004 | Monassevitch et al. | |
| D574,956 S | 8/2008 | Grim | |
| D586,915 S | 2/2009 | Grim | |
| 7,635,367 B2 | 12/2009 | Groiso | |
| 8,137,351 B2 | 3/2012 | Prandi | |

(Continued)

OTHER PUBLICATIONS

A brochure entitled "Solana FuseForce", Solana Surgical (1 page).

*Primary Examiner* — Andrew Yang
(74) *Attorney, Agent, or Firm* — Schwegman Lundberg & Woessner, P.A.

(57) ABSTRACT

An orthopedic staple includes a bridge portion having a pair of ends and a staple leg formed from a shape memory material connected to each of the pair of ends. The staple legs have a constrained position where the staple legs are generally parallel to one another and a relaxed position where the staple legs generally converge toward one another. Each of the staple legs has a protruding portion with a maximum leg thickness and a tip, with each of the staple legs increasing in thickness from the tip to the protruding portion. The bridge portion and each of the protruding portions define grasping portions therebetween that are configured to provide resistance to backout of the orthopedic staple.

21 Claims, 5 Drawing Sheets

(56) References Cited

U.S. PATENT DOCUMENTS

| | | |
|---|---|---|
| 8,211,109 B2 | 7/2012 | Groiso |
| 8,235,995 B2 | 8/2012 | Focht et al. |
| D675,734 S | 2/2013 | Cheney et al. |
| 8,372,075 B2 | 2/2013 | Groiso |
| 8,475,457 B2 | 7/2013 | Shano |
| 8,584,853 B2 | 11/2013 | Knight et al. |
| 8,596,514 B2 | 12/2013 | Miller et al. |
| 2005/0096660 A1 | 5/2005 | Allen |
| 2005/0273108 A1* | 12/2005 | Groiso ............... A61B 17/0642 606/75 |
| 2006/0058802 A1 | 3/2006 | Kofoed |
| 2008/0161808 A1 | 7/2008 | Fox |
| 2010/0087822 A1 | 4/2010 | Groiso |
| 2011/0276050 A1 | 11/2011 | Puricelli et al. |
| 2011/0295258 A9 | 12/2011 | Bhatnagar et al. |
| 2013/0026206 A1 | 1/2013 | Fox |
| 2013/0030437 A1 | 1/2013 | Fox |
| 2013/0030438 A1 | 1/2013 | Fox |
| 2013/0172929 A1 | 7/2013 | Hess et al. |
| 2013/0231667 A1 | 9/2013 | Taylor et al. |
| 2013/0331839 A1 | 12/2013 | Hester et al. |
| 2014/0018809 A1 | 1/2014 | Allen |

* cited by examiner

SHAPE MEMORY COMPRESSION STAPLE

BACKGROUND OF THE INVENTION

1. Field of the Invention

The present invention relates to orthopaedic devices, and, more particularly, to orthopaedic staples.

2. Description of the Related Art

Bone fractures are a common occurrence that can be treated with surgical intervention. One type of intervention commonly used to treat bone fractures is the use of bone staples to hold the bone fragments on either side of the fracture together. The implanted bone staple helps keep the bone fragments together so that they do not drift apart, allowing the bone to heal faster and reducing the risk of the fracture propagating through the bone.

To assist the bone healing process, compression bone staples are known that provide a compressive force to the bone fragments. The compressive force pushes the bone fragments together, which helps the body naturally mend the fragments back together and also provides a counter force to separation of the bone fragments by tensile forces experienced by the fragments. The compressive force from the bone staple can be provided to the bone fragments in a variety of ways.

For example, U.S. Pat. No. 5,053,038 describes a compression bone staple that includes springs for driving the bone together. The springs are a portion of the bone staple that connect the legs of the bone staple to a connecting portion running between the legs. However, due to the shape of the bone staple, compression of the bone tissue cannot be achieved along the entire length of the leg and will mostly be focused on the bent portion where the staple legs meet the springs. This is an undesirable compression pattern since it allows for tensile forces that are distanced from the compression center point to potentially pull the fragments apart. Other compression staples tend to focus their compressive force at the tips of the staples, which is also an undesirable compression pattern for similar reasons.

What is needed in the art is an orthopaedic staple that has improved compression characteristics over existing devices.

SUMMARY OF THE INVENTION

The present invention provides an orthopaedic staple with one or more staple legs formed from a shape memory material that can provide a more even compressive force distribution across the length of the one or more staple legs than known devices.

The invention in one form is directed to an orthopaedic staple that includes a bridge portion having a pair of ends and a staple leg formed from a shape memory material connected to each of the pair of ends. The staple legs have a constrained position where the staple legs are generally parallel to one another and a relaxed position where the staple legs generally converge toward one another. Each of the staple legs has a protruding portion with a maximum leg thickness and a tip, with each of the staple legs increasing in thickness from the tip to the protruding portion. The bridge portion and each of the protruding portions define grasping portions therebetween that are configured to provide resistance to backout of the orthopaedic staple.

The invention in another form is directed to an orthopaedic staple that includes a bridge portion having a first end and a second end, a first staple leg connected to the first end, and a second staple leg formed of a shape memory material connected to the second end. The second staple leg has a constrained position where the second staple leg and the first staple leg are substantially parallel to one another and a relaxed position where the second staple leg converges toward the first staple leg. The second staple leg has a protruding portion with a maximum leg thickness and a tip, with the second staple leg increasing in thickness from the tip to the protruding portion. The bridge portion and protruding portion define a grasping portion therebetween that is configured to provide resistance to backout of the orthopaedic staple.

The invention in yet another form is directed to a method of compressing bone tissue that includes providing an orthopaedic staple having a bridge portion with a pair of ends and a staple leg formed from a shape memory material connected to each of the pair of ends. The staple legs have a constrained position where the staple legs are generally parallel to one another and a relaxed position where the staple legs generally converge toward one another. Each of the staple legs has a protruding portion with a maximum leg thickness and a tip, with each of the staple legs increasing in thickness from the tip to the protruding portion. The bridge portion and each of the protruding portions define grasping portions therebetween that are configured to provide resistance to backout of the orthopaedic staple. The staple legs are held in the constrained position and a pair of staple leg holes are produced in the bone tissue. Each of the staple legs are placed in one of the staple leg holes and the staple legs are released.

An advantage of the present invention is that the increasing thickness of the one or more staple legs allows for compressive force to be delivered to the surrounding bone tissue along the length of the staple leg or legs.

Another advantage is that the grasping portion can provide resistance to the orthopaedic staple backing out of the bone.

Yet another advantage is that the grasping portion can also have a holder placed therein to hold the staple legs in the constrained position.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one embodiment of the invention and such exemplification is not to be construed as limiting the scope of the invention in any manner.

DETAILED DESCRIPTION OF THE INVENTION

Figure 1:
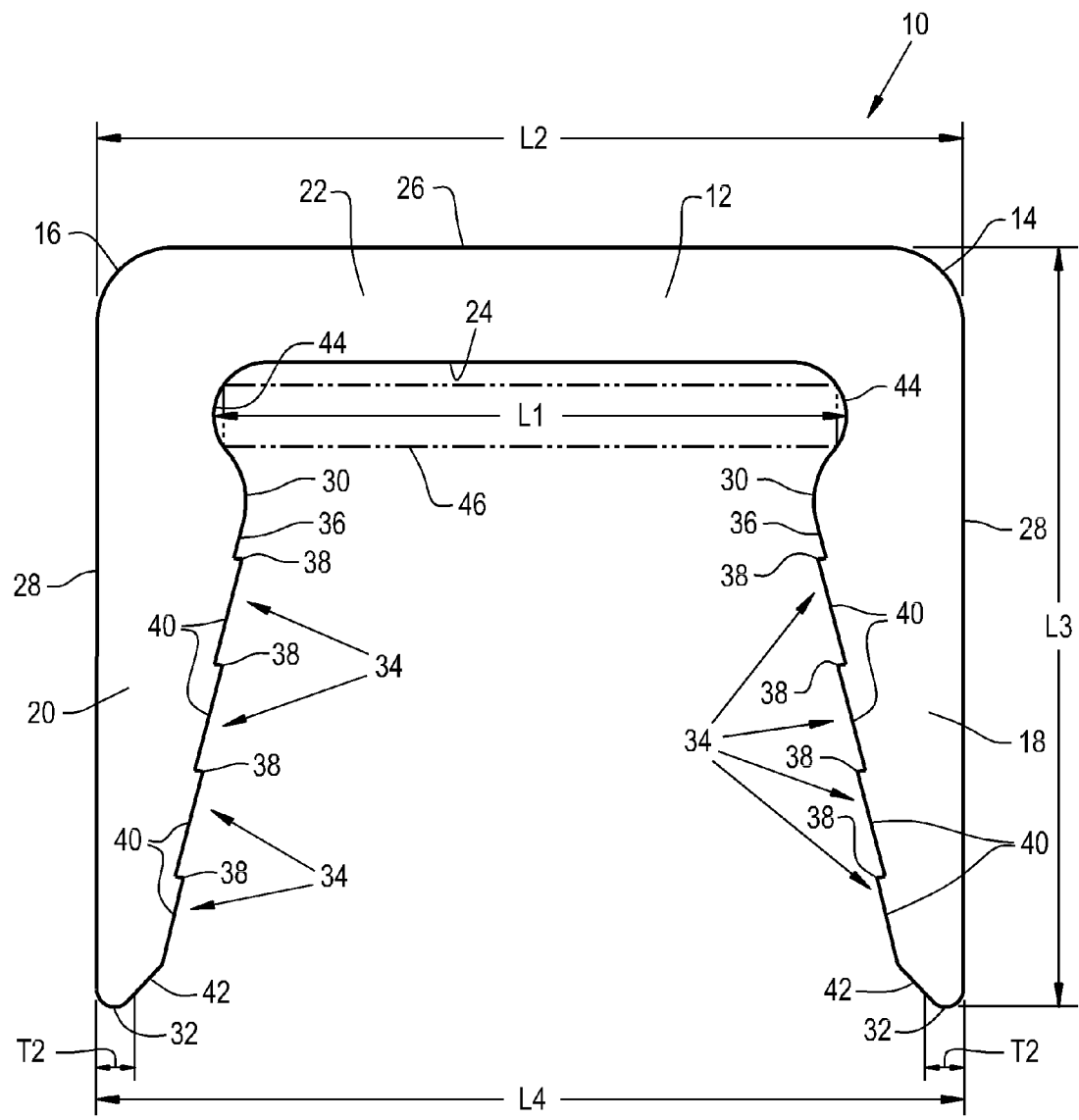
FIG. 1 is a front view of an embodiment of an orthopaedic staple according to the present invention being held in a constrained position.

Referring now to the drawings, and more particularly to FIG. 1, there is shown an embodiment of an orthopaedic staple 10 according to the present invention which generally includes a bridge portion 12 with a first end 14 and a second end 16, a first staple leg 18 connected to the first end 14 of the bridge portion 12, and a second staple leg 20 connected to the second end 16 of the bridge portion 12. As shown, the orthopaedic staple 10 is formed as a unitary component, i.e., the bridge portion 12, first staple leg 18 and second staple leg 20 are integrally formed together, but the orthopaedic staple 10 could also be formed as separable components that are connected together in any suitable fashion, if desired. As can be seen, the first end 14 and second end 16 are curved to allow for connection to the first staple leg 18 and second staple leg 20, respectively. The bridge portion 12 has a span 22 that extends between the first end 14 and second end 16 with an inner surface 24 and an opposing outer surface 26. As used herein, the term "inner" refers to an area surrounded by the orthopaedic staple 10 and the term "outer" refers to an area surrounding the orthopaedic staple 10, so that the inner surface 24 will face toward the area surrounded by the orthopaedic staple 10 and the outer surface 26 will face toward the area that surrounds the orthopaedic staple. These terms are used for convenience of description only and are not intended to limit the scope of the invention to specific configurations. As can be seen, the inner surface 24 and outer surface 26 of the span 22 are generally parallel to one another, but they could also be angled relative to one another if desired. The span 22 defines a span length L1 that can be varied to produce orthopaedic staples of various sizes. For example, the span length L1 can be between approximately 5 to 9 millimeters, but it should be appreciated that these values are exemplary only and not intended to limit the scope of the invention to any particular value of the span length L1. Similarly, the bridge portion 12 defines an end-to-end length L2 extending from the first end 14 to the second end 16 that can be varied to produce orthopaedic staples of various sizes. For example, the end-to-end length L2 can be between approximately 8 to 13 millimeters, but these values are exemplary only and not intended to limit the scope of the invention to any particular value of the end-to-end length L2. Since the orthopaedic staple 10 will be implanted within a patient for a potentially long time period, it is useful for the bridge portion 12 to be formed of a biocompatible material that produces medically acceptable levels of local and systemic toxicity during the implantation period. It is further useful if the bridge portion 12 is formed from a shape memory material, for reasons that will be described further below. Examples of acceptable materials can include, but are not limited to, nickel titanium alloys (Nitinol), titanium, cobalt chrome, stainless steel, tantalum, tungsten, polyether ether ketone (PEEK), and ultra-high molecular weight polyethylene (UHMWPE). The bridge portion 12, and other elements of the orthopaedic staple 10, can be formed by any manufacturing process that allows for a suitable shape to be formed, such as casting, molding, machining, etching, etc.

A first staple leg 18 is connected to the first end 14 of the bridge portion 12 and a second staple leg 20 is connected to the second end 16 of the bridge portion 12. As shown in the figures, the first staple leg 18 and second staple leg 20 are essentially mirror images of each other, i.e., the orthopaedic staple 10 looks identical in both the front view and the rear view. The first staple leg 18 and second staple leg 20 are shown as mirror images of each other only to illustrate one embodiment of the present invention, but it is contemplated that the two legs of an orthopaedic staple could be non-mirror images of each other according to the present invention. For convenience of description, the first staple leg 18 and the second staple leg 20 will be described together as "the pair of staple legs 18, 20" or simply "the staple legs 18, 20" since they share common features that are mirrored, but it should be understood that such common features are not required by the present invention.

Figure 2:
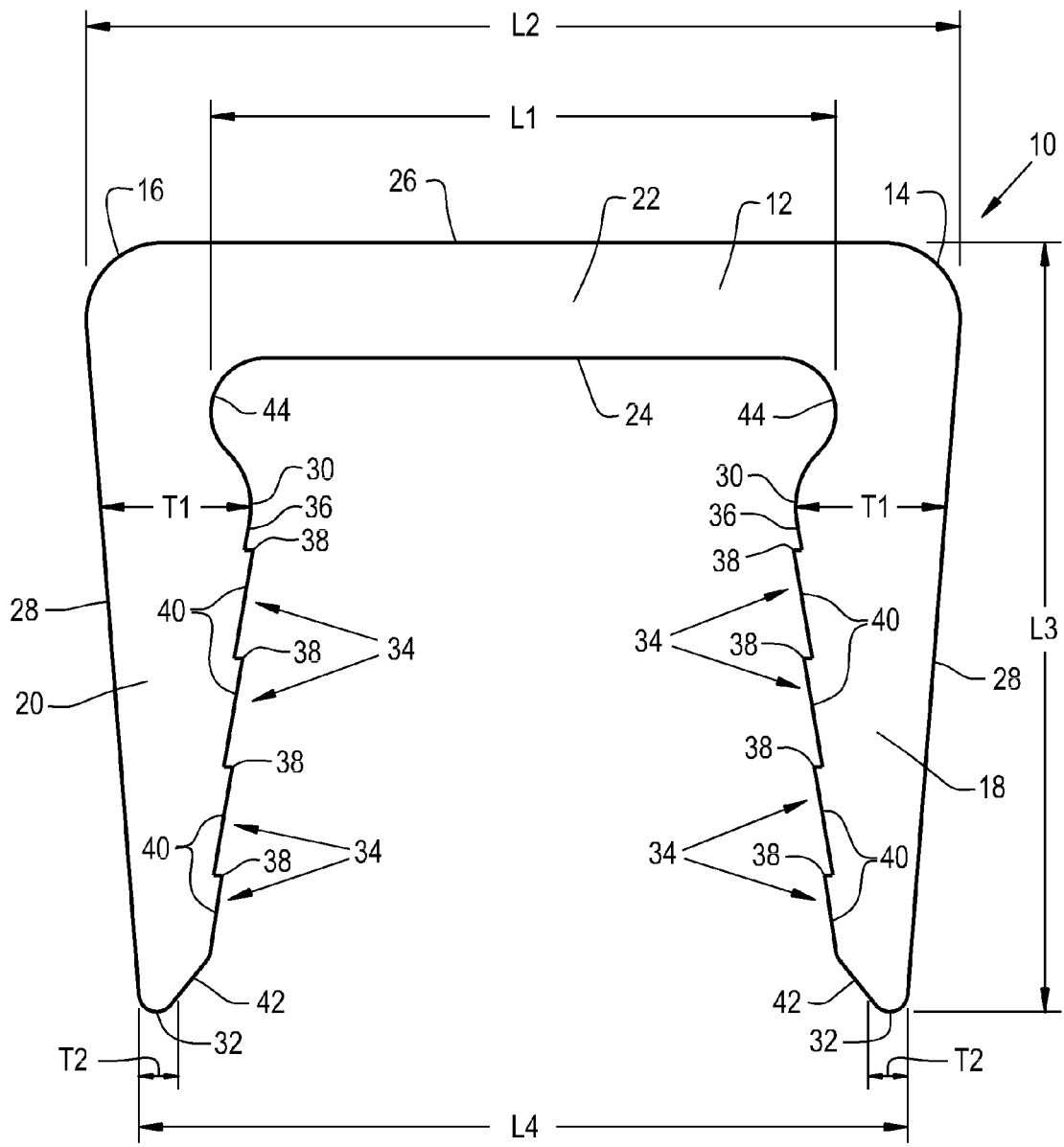
FIG. 2 is a front view of the orthopaedic staple shown in FIG. 1 that is in a relaxed position.

As can be seen in FIG. 1, the staple legs 18, 20 are held in a constrained position where outer leg surfaces 28 of the staple legs 18, 20 are generally parallel to each other. As used herein, "generally parallel" refers to axes defined by the outer leg surfaces 28 both being perpendicular to a common line, defined here by the outer surface 26 of the span 22, or being slightly non-perpendicular in that one or both of the outer leg surfaces 28 form an angle of about 88 to 92 degrees relative to the outer surface 26 of the span 22. As shown, the outer leg surfaces 28 are substantially flat, i.e., the outer leg surfaces 28 form a single, uninterrupted plane, but could also incorporate textural features, such as ridges, or be curved. The staple legs 18, 20 are formed of a shape memory material, such as Nitinol, so that they are elastic below their transformation temperature but will return to their originally formed shape above their transformation temperature. The staple legs 18, 20 can be formed of the same shape memory material so they have similar material properties, or could be formed from different shape memory materials so that the staple legs 18, 20 have different material properties. The shape memory material forming the staple legs 18, 20 can have a transformation temperature that is below body temperature (which can be considered to be about 37 degrees Celsius), so implantation of the orthopaedic staple 10 in the patient allows the patient's body to heat the staple legs 18, 20 above the transformation temperature and causes the staple legs 18, 20 to spontaneously revert toward their originally formed shape, which can be referred to as a relaxed position. In the relaxed position, the staple legs 18, 20 generally converge toward one another, as can be seen in FIG. 2. As used herein, "generally converge" refers to the tendency of the bulk material of each staple leg 18, 20 to spontaneously migrate toward the bulk material of the other staple leg 18, 20 in the relaxed position. This property of the staple legs 18, 20 to spontaneously assume their relaxed position upon heating to a temperature above their transformation temperature allows for the staple legs 18, 20 to apply compressive force to bone tissue between the staple legs 18, 20. Using a material such as Nitinol to form the staple legs 18, 20 can allow for the outer leg surfaces 28 to experience a significant angular change between the constrained and relaxed positions, relative to the outer surface 26 of the span 22. During the transition between the constrained and the relaxed positions, each outer leg surface 28 can experience an angle change, relative to the outer surface 26 of the span 22, of between about 2 to 12 degrees. For example, if the outer leg surfaces 28 each form a 90 degree angle relative to the outer surface 26 of the span 22 in the constrained position, the outer leg surfaces 28 can each form an angle of between 78 and 88 degrees relative to the outer surface 26 of the span 22 in the relaxed position. It should be appreciated that the angle change experienced by the outer leg surfaces 28, which defines an angular change or movement of the staple legs 18, 20, between the constrained and relaxed positions can be altered to adjust the compressive forces that are applied to the bone tissue and the configuration that the staple legs 18, 20 will assume when implanted into the bone tissue.

Figure 3:
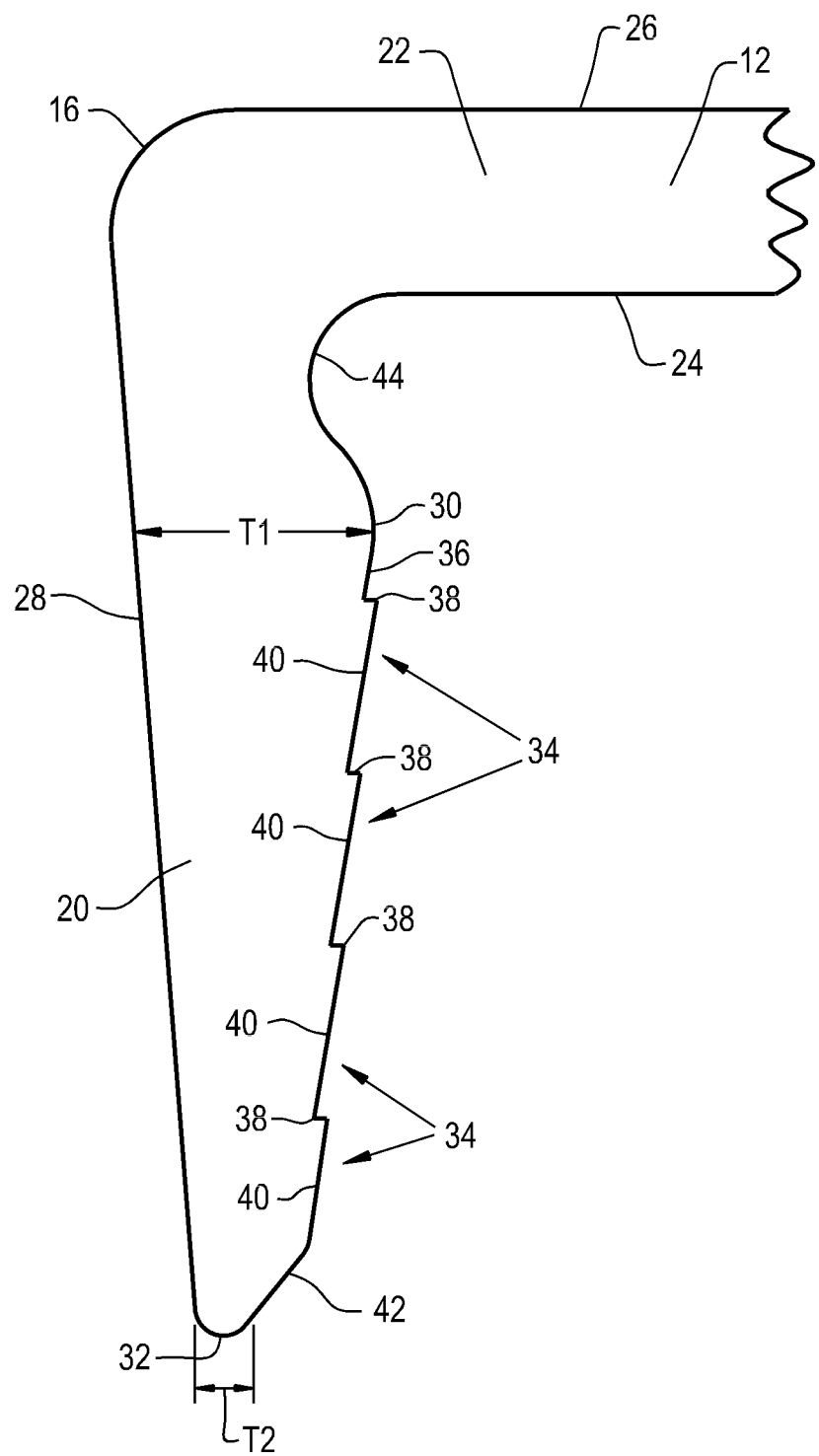
FIG. 3 is a front view of the orthopaedic staple shown in FIG. 2 with portions broken away.

Referring now to FIGS. 2 and 3, the orthopaedic staple 10 is shown with the staple legs 18, 20 in the relaxed position and converging toward one another. Each of the staple legs 18, 20 define a staple length L3 and have a varying cross-sectional thickness along the staple length L3. The staple length L3 can have varying values to produce orthopaedic staples of various sizes, with exemplary values being between about 9 and 13 millimeters. As can be seen, the staple legs 18, 20 each have a protruding portion 30 with a maximum leg thickness T1 that is adjacent to the respective ends 14, 16 of the bridge portion 12 and a tip 32 with a minimum leg thickness T2 that is the most distal portion of the staple legs 18, 20 from the respective ends 14, 16. The tips 32, as shown, have a rounded shape with an arc length that correlates to the minimum leg thickness T2, but could also have an angular shape if desired. As used herein, the thickness of the staple legs 18, 20 are described as increasing between the tips 32 and the protruding portions 30 in a direction from the tips 32 toward the protruding portions 30. The increase in thickness can be stepwise, as shown, or can be gradual. When the thickness increase is stepwise, one or more serrations 34 can be formed on inner leg surfaces 36 of one or both of the staple legs 18, 20 that define the stepwise increases and produce frictional forces to give the orthopaedic staple 10 better backout resistance. The serrations 34 can each have a transition area 38 where the thickness of the staple legs 18, 20 decreases before transitioning into a serration valley 40 where the thickness of the staple legs 18, 20 increases linearly, which can be more clearly seen in FIG. 3. If serrations 34 are included on one or both of the inner leg surfaces 36, the number and length of the transition areas 38 and serration valleys 40 can be adjusted as desired to produce a desired amount of frictional forces between the orthopaedic staple 10 and the bone tissue. As shown in FIGS. 1-3, the inner leg surfaces 36 each have four serrations 34 included thereon. Each staple leg 18, 20 can also have a thickening region 42 which is a step of thickness increase that has a significantly greater increase of thickness compared to the serrations 34. As can be seen, the thickening regions 42 can be located between the serration 34 closest to the tips 34 and the tips 34.

The protruding portions 30 can have a curved cross-section defined about the maximum leg thickness T1 to produce a curved inner surface. Grasping portions 44 are therefore defined between the bridge portion 12 and the protruding portions 30 which allow for bone tissue to be pushed or held in a space defined between the protruding portions 30 and the bridge portion 12 to provide resistance to backout of the orthopaedic staple 10 and lock underneath the cortical shell of a bone, which is described below. The grasping portions 44, as shown, have a curved cross-sectional shape that are significantly more arced than the protruding portions 30 and extend in a direction opposing the protruding portions 30. For example, when the curved cross-sections of the protruding portions 30 roughly define arcs of circles with a radius of 1, the curved cross-sections of the grasping portions 44 roughly define arcs of circles with a radius of between 0.65 and 0.75 extending between the inner surface 24 of the bridge portion 12 and the protruding portions 30 which gives the grasping portions 44 a "sharper" curved inner surface than the protruding portions 30. A ratio between the radii of the curved cross-sections of the protruding portions 30 and the grasping portions 44 can be adjusted, as desired, to give differently shaped grasping portions 44 that can provide more or less space between the protruding portions 30 and bridge portion 12, with exemplary values of the ratio being between 5:4 and 2:1. As can be seen in FIG. 1, the grasping portions 44 can also allow for a holder 46 to be placed against the curved inner surfaces of the grasping portions 44 that can spread and hold the staple legs 18, 20 in their constrained position. The holder 46 can have any shape that allows for the grasping portions 44 to be forced away from each other to assume the constrained position and be held in the constrained position until being released.

As is known, bones include both cortical bone tissue and cancellous bone tissue. Cortical bone tissue has a significantly higher density and strength compared to cancellous bone, and forms the outer layer of bones. The outer layer of cortical bone tissue can also be referred to as "the cortical shell." Cancellous bone tissue, on the other hand, is fairly porous and spongy, allowing for it to be more easily compressed than cortical bone tissue. When the orthopaedic staple 10 according to the present invention is used to compress bone fragments together, the increasing thickness of the staple legs 18, 20 from the tips 34 toward the protruding portions 30 force proximal bone fragments together, compressing the cancellous bone tissue. Once the orthopaedic staple 10 has been advanced into the bone fragments so that the protruding portions 30 are within the cancellous bone tissue, the protruding portions 30 maximally compress the soft, spongy cancellous bone tissue together, due to the maximum thickness of the staple legs 18, 20 at the protruding portions 30. The cortical shell will experience some compressive change during insertion of the orthopaedic staple 10, but it will be much less than the compressive change experienced by the cancellous bone tissue. The protruding portions 30 can therefore compress together the cancellous bone tissue underneath the cortical shell so that the protruding portions 30 will be forced underneath the cortical shell. The cortical shell therefore fills in the grasping portions 44 when the orthopaedic staple 10 is fully inserted and acts a "lock" to provide resistance to the staple legs 18, 20 being pulled out by interfering with upward motion of the protruding portions 30, which are locked underneath the cortical shell. It should be appreciated that when only one of the staple legs has a protruding portion and a grasping portion, locking under the cortical shell can still occur due to compression of the cancellous bone tissue by the protruding portion and filling of the grasping portion by the cortical shell.

When the staple legs 18, 20 are in the relaxed position, the staple legs 18, 20 have a tip-to-tip length L4 that is defined by a distance between the tips 34 of the staple legs 18, 20. The configuration of the staple legs 18, 20 can be changed so that different tip-to-tip length L4 values can be achieved to produce orthopaedic staples of various sizes. The tip-to-tip length L4 can be, for example, between about 6 and 11 millimeters, depending on the desired size of the orthopaedic staple 10. It should be appreciated the tip-to-tip length L4 of the staple legs 18, 20 will change between the constrained and relaxed positions due to angular changes of the staple legs 18, 20. To give the orthopaedic staple 10 the desired compression characteristics at various sizes, a sizing ratio of the end-to-end length L2, span length L1, staple length L3, and tip-to-tip length L4 can be defined as L2:L1:L4:L3, which can be utilized to determine how changing the size of one or more values should affect the other values. Possible sizing ratios that can be utilized to determine the proper values for the lengths can be 140-155: 95-105:110-125: 120-170, but it should be understood that these values are exemplary only and not intended to limit the scope of the invention in any manner.

Figure 4:
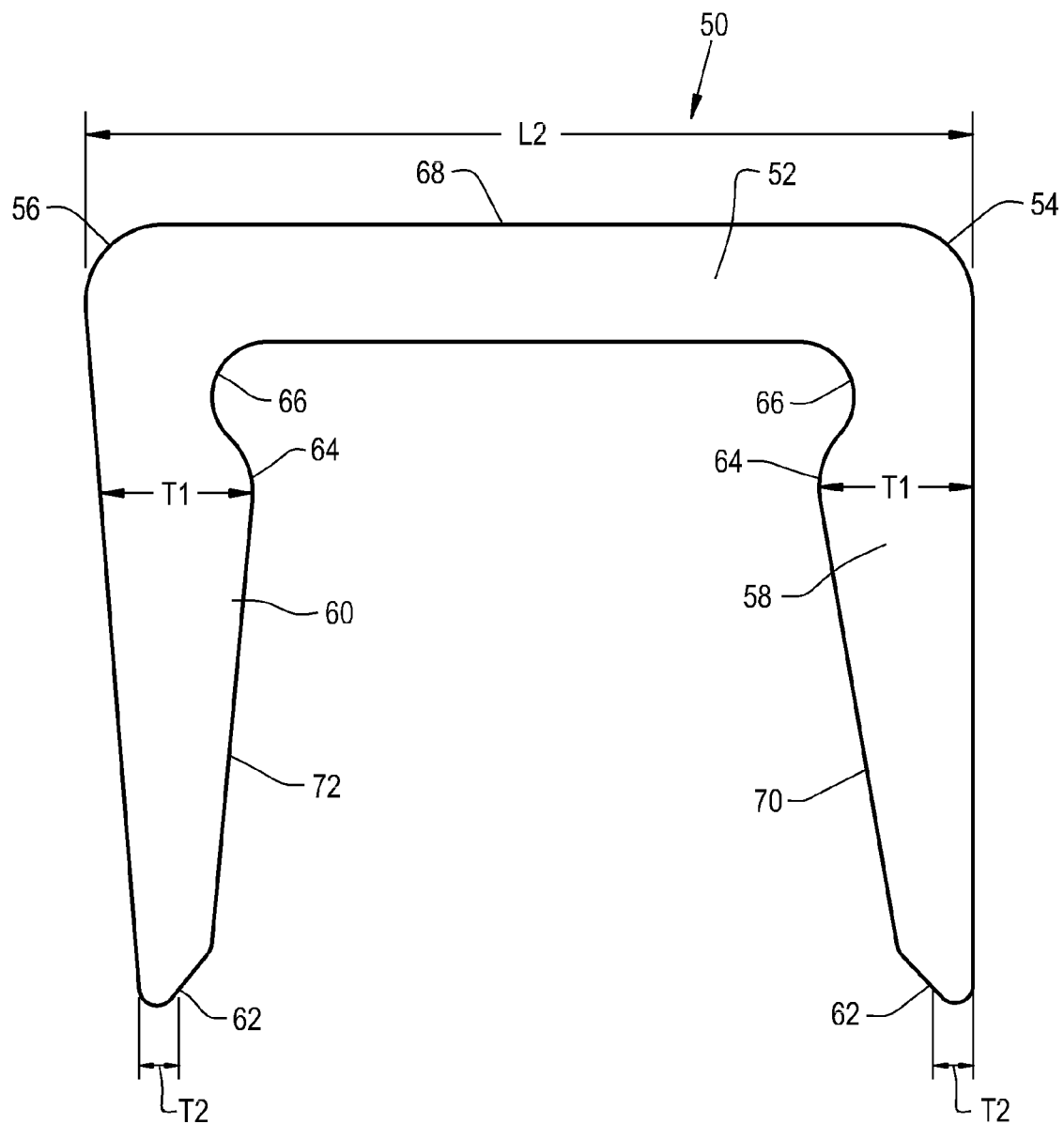
FIG. 4 is a front view of another embodiment of an orthopaedic staple according to the present invention in a relaxed position.

Referring now to FIG. 4, another embodiment of an orthopaedic staple 50 according to the present invention is shown that includes a bridge portion 52 with a first end 54 and a second end 56, a first staple leg 58 connected to the first end 54 and a second staple leg 60 formed of a shape memory material connected to the second end 56. The orthopaedic staple 50 shown in FIG. 4 is structurally similar to the orthopaedic staple 10 shown in FIGS. 1-3, in that the second staple leg 60, and optionally the first staple leg 58, can include a tip 62, a protruding portion 64, and a grasping portion 66 defined between the bridge portion 52 and protruding portion 64. However, rather than having both staple legs 58, 60 formed of a shape memory material, only the second staple leg 60 of orthopaedic staple 50 is formed from a shape memory material with a constrained and relaxed position while the first staple leg 58 can be formed of any material. In this embodiment, both the first staple leg 58 and second staple leg 60 are perpendicular to an outer surface 68 of the bridge portion 52 in the constrained position, but only the second staple leg 60 will converge toward an inner surface 70 of the first staple leg 58 in the relaxed position, i.e., the first staple leg 58 does not spontaneously revert to a relaxed position after a force applied to the first staple leg 58 is released. Such an embodiment allows for compressive force applied to bone tissue to originate along an inner surface 72 of the second staple leg 60 in the relaxed position, which may be desirable in certain fracture patterns. To achieve sufficient compression of bone tissue, the second staple leg 60 can be configured to have an angle change of between about 2 to 15 degrees when moving from the constrained position to the relaxed position.

Figure 5:
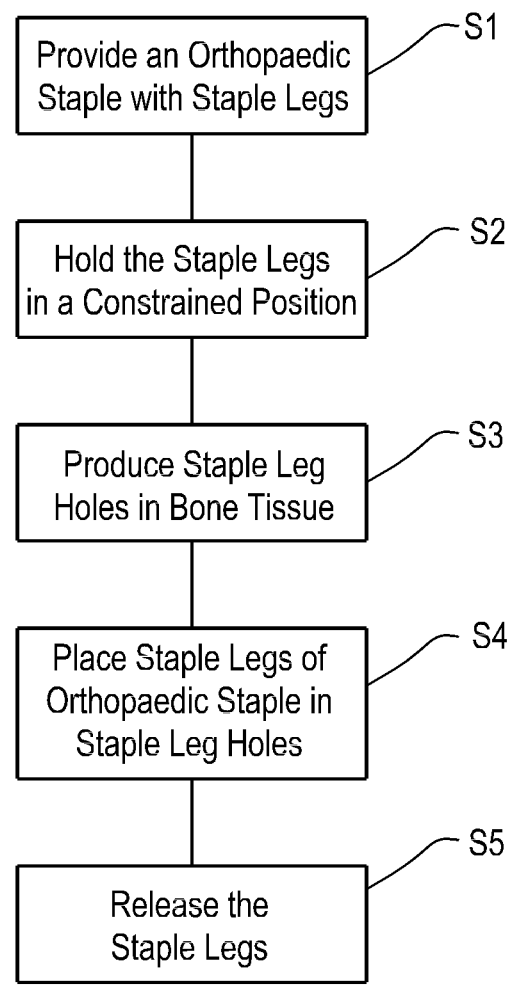
FIG. 5 is a flow chart of an embodiment of a method of compressing bone tissue according to the present invention.

To use the previously described orthopaedic staple 10 and 50, and now referring to FIG. 5, the orthopaedic staples 10, 50 are provided S1 and held S2 in their respective constrained positions. The orthopaedic staples 10, 50 can be held in their respective constrained position by the holder 46 previously described, or any holder that is capable of holding the staple legs 18, 20 and 58, 60 generally parallel to each other. Staple leg holes are produced S3 in bone tissue that is to be compressed. The staple leg holes can be produced on opposing sides of a fracture, so that compressive force applied to the bone tissue by the orthopaedic staples 10, 50 will compress the bone tissue toward the fracture. The staple leg holes can be spaced apart by a distance that is roughly equivalent to the end-to-end length L2 of the orthopaedic staples 10, 50 so that the orthopaedic staples 10, 50 can be placed in the staple leg holes in the constrained position. The staple leg holes can be produced with a diameter that is lower than the maximum leg thickness T1 of one or more of the staple legs 18, 20, 58, 60 of the respective orthopaedic staple 10, 50 being implanted. It is useful if one or more of the staple leg holes produced has a diameter that is roughly equivalent to the minimum leg thickness T2 defined at one or more of the tips 34, 62 of the staple legs 18, 20, 58, 60 so that the staple leg hole is undersized compared to one or more of the staple legs 18, 20, 58, 60. This undersizing of one or more of the staple leg holes can usefully allow for the compressive force applied to the bone tissue by one or more of the staple legs 18, 20, 58, 60 to be more evenly distributed across the staple legs 18, 20, 58, 60. The staple legs 18, 20 and 58, 60 are placed S4 in the produced staple leg holes, with one staple leg going in each staple leg hole, and the staple legs 18, 20 and 58, 60 are released S5 so that the staple legs 18, 20, 58, 60 can attempt to revert to their relaxed state in the bone tissue, which produces compression on the bone tissue. The increased thickness of the staple legs 18, 20 and 58, 60 from the tips 34, 62 to the protruding portions 30, 64 compensates for the tendency of the compressive force applied by the staple legs 18, 20 and 58, 60 in the relaxed position to be focused at the tips 34, 62, and can produce compression along a greater proportion of the lengths of the staple legs 18, 20 and 58, 60 that contact the bone tissue. It should be appreciated that the above steps S1-S5 of the method according to the present invention can be performed in any order that allows for the method to be accomplished using any tools or procedures.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic staple assembly, comprising:
    an orthopaedic staple, comprising:
        a bridge portion having a pair of ends; and
        a staple leg formed from a shape memory material connected to each of said pair of ends, said staple legs having a constrained position where said staple legs are generally parallel to one another and a relaxed position where said staple legs generally converge toward one another, each of said staple legs including a tip and a protruding portion, the protruding portion of each of said staple legs forming a first curved inner surface of the staple leg that encompasses a maximum leg thickness of the staple leg, each of said staple legs increasing in thickness from said tip to said protruding portion, said bridge portion and each of said protruding portions defining a grasping portion therebetween configured to provide resistance to backout of said orthopaedic staple, wherein the grasping portion of each of said staple legs forms a second curved inner surface of the staple leg that extends in a direction opposing the first curved inner surface of the staple leg; and
    a holder,
    wherein the staple legs are in said constrained position, and wherein the holder is positioned against the second curved inner surface of each of said staple legs to keep said staple legs in said constrained position.

2. The orthopaedic staple assembly according to claim 1, wherein each of said staple legs has an outer leg surface that is substantially flat.

3. The orthopaedic staple according to claim 1, wherein for each of said staple legs the first curved inner surface has a first radius and the second curved inner surface has a second radius, the ratio of the first radius to the second radius for each of said staple legs ranging from 5:4 to 2:1.

4. The orthopaedic staple assembly according to claim 1, wherein said staple legs are configured to move at least 5 degrees between said constrained position and said relaxed position.

5. The orthopaedic staple assembly according to claim 4, wherein said staple legs are configured to move at least 10 degrees between said constrained position and said relaxed position.

6. The orthopaedic staple assembly according to claim 1, wherein said grasping portions are configured to allow locking of said protruding portions underneath a cortical shell after insertion of said orthopaedic staple.

7. The orthopaedic staple assembly according to claim 1, wherein each of said staple legs increases in thickness in a stepwise manner between said tip and said protruding portion.

8. The orthopaedic staple assembly according to claim 7, wherein a serration formed in each of said staple legs defines at least one of said increases in thickness.

9. An orthopaedic staple, comprising:
a bridge portion having a pair of ends; and
a staple leg formed from a shape memory material connected to each of said pair of ends, said staple legs having a constrained position where said staple legs are generally parallel to one another and a relaxed position where said staple legs generally converge toward one another, each of said staple legs including a tip and a protruding portion, the protruding portion of each of said staple legs forming a first curved inner surface of the staple leg that encompasses a maximum leg thickness of the staple leg, each of said staple legs increasing in thickness from said tip to said protruding portion, said bridge portion and each of said protruding portions defining a grasping portion therebetween configured to provide resistance to backout of said orthopaedic staple, wherein the grasping portion of each of said staple legs forms a second curved inner surface of the staple leg that extends in a direction opposing the first curved inner surface of the staple leg
wherein for each of said staple legs the first curved inner surface has a first radius and the second curved inner surface has a second radius, the ratio of the first radius to the second radius for each of said staple legs ranging from 5:4 to 2:1.

10. An orthopaedic staple, comprising:
a bridge portion having a pair of ends; and
a staple leg connected to each of said pair of ends and formed of a shape memory material, said staple legs having a constrained position where said staple legs are generally parallel to one another and a relaxed position where said staple legs converge toward one another, each of said staple legs including a tip and a protruding portion that provides the staple leg with a maximum leg thickness, the protruding portion of each of said staple legs forming a first curved inner surface of the staple leg having a first radius, each of said staple legs increasing in thickness from said tip to said protruding portion, said bridge portion and each of said protruding portions defining a grasping portion therebetween configured to provide resistance to backout of said orthopaedic staple, wherein the grasping portion of each of said staple legs forms a second curved inner surface of the staple leg having a second radius, and wherein the ratio of the first radius to the second radius for each of said staple legs ranges from 5:4 to 2:1.

11. The orthopaedic staple according to claim 10 in combination with a holder and with said staple legs in said constrained position, the holder positioned against the second curved inner surface of each of said staple legs to keep said staple legs in said constrained position.

12. The orthopaedic staple according to claim 10, wherein each of said staple legs has an outer leg surface that is substantially flat.

13. The orthopaedic staple according to claim 10, wherein said staple legs are configured to move at least 5 degrees between said constrained position and said relaxed position.

14. The orthopaedic staple according to claim 13, wherein said staple legs are configured to move at least 10 degrees between said constrained position and said relaxed position.

15. The orthopaedic staple according to claim 10, wherein said grasping portions are configured to allow locking of said protruding portions underneath a cortical shell after insertion of said orthopaedic staple.

16. The orthopaedic staple according to claim 10, wherein each of said staple legs increases in thickness in a stepwise manner between said tip and said protruding portion.

17. The orthopaedic staple according to claim 16, wherein a serration formed in each of said staple legs defines at least one of said increases in thickness.

18. A method of compressing bone tissue, comprising the steps of:
providing an orthopaedic staple having a bridge portion with a pair of ends and a staple leg formed from a shape memory material connected to each of said pair of ends, said staple legs having a constrained position where said staple legs are generally parallel to one another and a relaxed position where said staple legs generally converge toward one another, each of said staple legs including a tip and a protruding portion that provides the staple leg with a maximum leg thickness, each of said staple legs increasing in thickness from said tip to said protruding portion, said bridge portion and each of said protruding portions defining a grasping portion therebetween configured to provide resistance to backout of said orthopaedic staple;
holding said staple legs in said constrained position which includes positioning a holder in each of said grasping portions so as to force said staple legs into said constrained position;
producing a pair of staple leg holes in said bone tissue;
placing each of said staple legs in one of said pair of staple leg holes; and
releasing said staple legs.

19. The method according to claim 18, wherein the protruding portion of each of said staple legs forms a first curved inner surface of the staple leg that encompasses the maximum leg thickness of the staple leg.

20. The method according to claim 19, wherein the grasping portion of each of said staple legs forms a second curved inner surface of the staple leg that extends in a direction opposing the first curved inner surface of the staple leg.

21. The orthopaedic staple according to claim 20, wherein for each of said staple legs the first curved inner surface has a first radius and the second curved inner surface has a second radius, the ratio of the first radius to the second radius for each of said staple legs ranging from 5:4 to 2:1.

* * * * *